United States Patent [19]
Kohayakawa et al.

[11] Patent Number: 4,820,037
[45] Date of Patent: Apr. 11, 1989

[54] APPARATUS FOR MEASURING THE REFRACTIVE POWER OF AN EYE

[75] Inventors: Yoshimi Kohayakawa, Yokohama; Kazuhiro Matsumoto, Kawasaki, both of Japan

[73] Assignee: Canon Kabushiki Kaisha, Tokyo, Japan

[21] Appl. No.: 232,558

[22] Filed: Aug. 15, 1988

Related U.S. Application Data

[63] Continuation of Ser. No. 814,966, Dec. 31, 1985, abandoned.

[30] Foreign Application Priority Data

Jan. 10, 1985 [JP] Japan .................. 60-2494
Jun. 14, 1985 [JP] Japan ................ 60-129399
Jul. 5, 1985 [JP] Japan ................ 60-146647

[51] Int. Cl.$^4$ ............................ A61B 3/10; A61B 3/14
[52] U.S. Cl. ..................................... 351/211; 351/206
[58] Field of Search ................... 351/206, 211; 354/62

[56] References Cited

U.S. PATENT DOCUMENTS 4,306,778 12/1981 Wada et al. ................... 351/211
4,376,573 3/1983 Matsumura et al. .............. 351/211
4,410,243 10/1983 Fürste ............................ 351/211

FOREIGN PATENT DOCUMENTS 56-161031 5/1980 Japan .

Primary Examiner—Rodney B. Bovernick
Attorney, Agent, or Firm—Fitzpatrick, Cella, Harper & Scinto

[57] ABSTRACT

An apparatus for measuring the refractive power of an eye has a target projecting system for projecting a target light beam onto the fundus of an eye to be examined through a predetermined region of the pupil of the eye to be examined, and a light-receiving optical system for receiving a light beam reflected by the eye fundus in at least three meridian directions through a region of the pupil of the eye to be examined different from the predetermined region. The light-receiving optical system includes a plurality of image rotating prisms for converting into a predetermined direction the direction of displacement to each meridian direction of the light beam reflected by the eye fundus produced by the difference in the refractive power of the eye to be examined. A light detecting device has a direction of light detection coincident with the predetermined direction and detects the light-position of the light beam reflected by the eye fundus which depends on the refractive power of the eye to be examined.

15 Claims, 29 Drawing Sheets

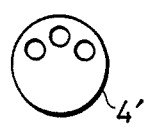
FIG. 8
FIG. 9
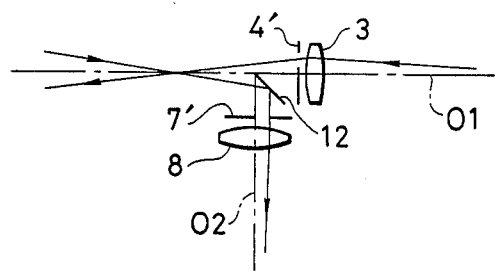
FIG. 10
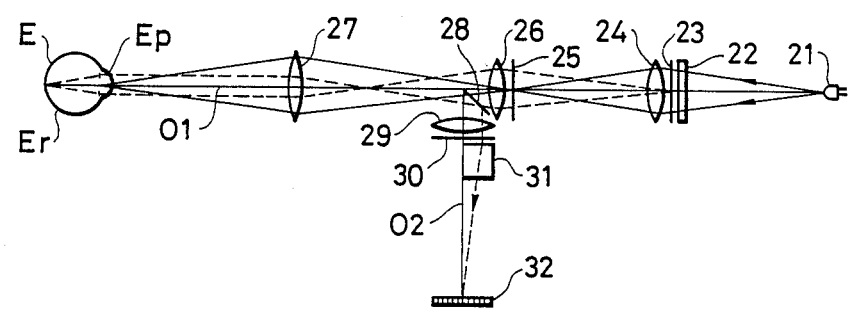
FIG. 11
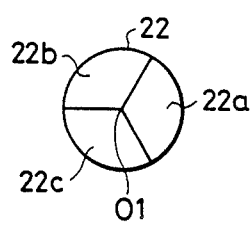
FIG. 12
FIG. 13 FIG. 14 FIG. 15
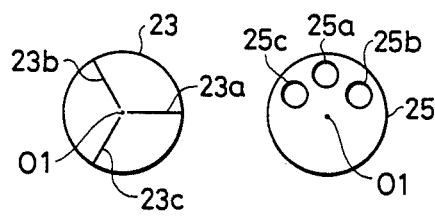
FIG. 16
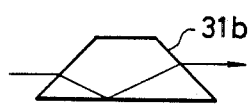
FIG. 17
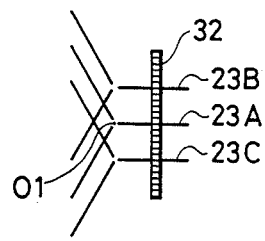
FIG. 18
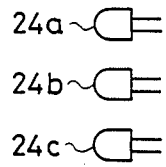

APPARATUS FOR MEASURING THE REFRACTIVE POWER OF AN EYE

This application is a continuation of application Ser. No. 814,966 filed Dec. 31, 1985, now abandoned.

BACKGROUND OF THE INVENTION

1. Field of the Invention

This invention relates to an eye refractive power measuring apparatus used in ophthalmic hospitals or by opticians to measure the degree of spherical refraction, the degree of astigmatic refraction, the angle of astigmatism, etc. of an eye.

2. Description of the Prior Art

Heretofore, an eye refractive power measuring apparatus of this type has generally been such that a light from a light source is directed to an eye to be examined, the image of the light source is projected onto the fundus of the eye to be examined, and the reflected light from the eye fundus is received by three light-receiving elements disposed in at least three meridian directions, whereby measurement of the refractive power of the eye in each meridian direction is accomplished. Such apparatus is disclosed, for example, in applicant's U.S. application Ser. No. 755,362, but this apparatus requires at least three light-receiving elements different in direction of disposition, and this has led to the structural complexity and high cost of the apparatus.

SUMMARY OF THE INVENTION

It is an object of the present invention to provide an apparatus for measuring the refractive power of an eye which is simple in the arrangement and structure of light-position detecting means and is therefore inexpensive.

It is another object of the present invention to provide an apparatus for measuring the refractive power of an eye which has no movable part and can accomplish stable measurement.

It is still another object of the present invention to provide an apparatus for measuring the refractive power of an eye which can measure the refractive power of an eye by the use of the scanning lines of a TV camera used for the observation of an eye to be examined.

BRIEF DESCRIPTION OF THE DRAWINGS

FIGS. 8 and 9 are front views of modifications of the three-aperture stops.

FIG. 10 shows the optical arrangement of another embodiment of the present invention.

FIG. 11 shows the optical arrangement of a different embodiment of the present invention.

FIG. 12 is a front view of a deflecting prism.

FIG. 13 is a front view of a slit plate.

FIG. 14 is a front view of an aperture stop having three openings in the upper half thereof.

FIG. 15 is a front view of an aperture stop having three openings in the lower half thereof.

FIG. 16 illustrates the state of a light beam passing through an image rotating prism.

FIG. 17 shows the distribution of slit images on a linear photosensor array.

FIG. 18 shows the arrangement of three light sources in another embodiment of the present invention.

DESCRIPTION OF THE PREFERRED EMBODIMENTS

Figure 1:
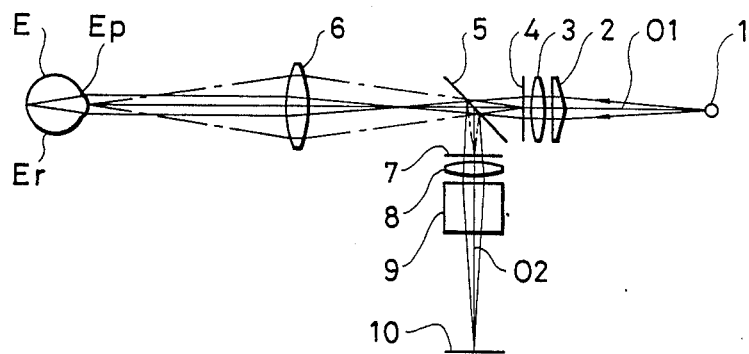
FIG. 1 shows the optical arrangement of a first embodiment of the present invention.

The present invention will hereinafter be described in detail with respect to some embodiments thereof shown in the drawings.

Referring to FIG. 1 which shows a first embodiment of the present invention, a deflecting prism 2, and lens 3, a first three-aperture stop 4, an apertured mirror 5 and an objective 6 are disposed in succession from a light source 1 side on an optical axis 01 passing through the light source 1 and an eye E to be examined, and a second three-aperture stop 7, a lens 8, an image rotating prism 9 and a light-receiving element 10 are arranged in succession on an optical axis 02 on the reflection side of a light beam travelling from the eye E to be examined toward the light source 1 by the apertured mirror 5. The light source 1 and the light-receiving surface of the light-receiving element 10 are substantially optically conjugate with respect to the fundus Er of an emmetropia and the first and second three-aperture stops 4 and 7 are substantially optically conjugate with the pupil Ep of the eye E to be examined.

Figure 2:
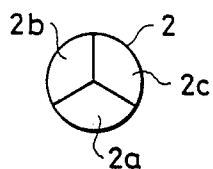
FIG. 2 is a front view of a deflecting prism.
Figure 3:
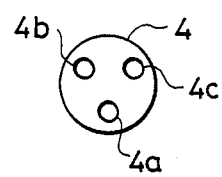
FIGS. 3 and 4 are front views of three-aperture stops.
Figure 4:
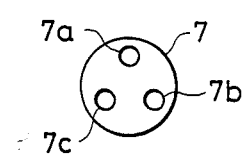
Figure 5:
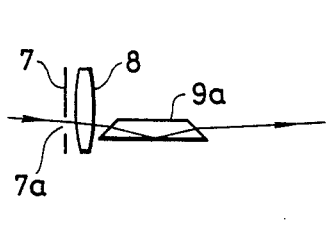
FIG. 5 illustrates the image rotation by an image rotating prism.
Figure 6:
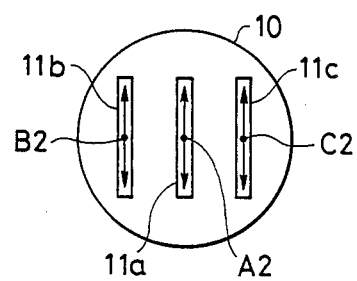
FIG. 6 is a plan view of a light-receiving element.

The deflecting prism 2, as shown in FIG. 2, comprises three wedge prisms 2a, 2b and 2c, which correspond to the apertures 4a, 4b and 4c, respectively, of the first three-aperture stop 4 shown in FIG. 3, and the apertured mirror 5 is provided with three apertures corresponding to the apertures 4a, 4b and 4c of the first three-aperture stop 4. Instead of the deflecting prism 2 and the single light source 1, three light sources 1 may be used. The apertures 4a, 4b and 4c of the first three-aperture stop 4 are substantially symmetrical with the aperture 7a, 7b and 7c of the second three-aperture stop 7 shown in FIG. 4 with respect to the center of the stop, i.e., the center of the pupil Ep. The image rotating prism 9 comprises three prisms 9a, 9b and 9c (of which the prisms 9b and 9c are not shown), and as partly shown in FIG. 5, these prisms are disposed while being rotated by a predetermined angle correspondingly to the apertures 7a, 7b and 7c of the second three-aperture stop 7. The light-receiving element 10, as shown in FIG. 6, has three one-dimensional light-position sensors 11a, 11b and 11c arranged parallel to one another.

Accordingly, a light beam emitted from the light source 1 passes through the deflecting prism 2, the lens 3, the first three-aperture stop 4, the apertured mirror 5 and the objective 6 to the eye E to be examined. The light reflected by the eye fundus Er passes through the objective 6, is reflected toward the optical axis 02 by the apertured mirror 5 and passes through the second three-aperture stop 7, the lens 8 and the image rotating prism 9 to the light-receiving surface of the light-receiving element 10.

Figure 7:
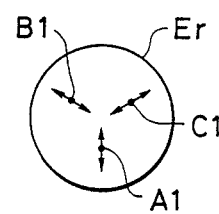
FIG. 7 illustrates the light source image on the fundus of an eye.

FIG. 7 shows light source images A1, B1 and C1 projected onto the eye fundus Er through the apertures 4a, 4b and 4c of the first three-aperture stop 4 in the embodiment of FIG. 1, and arrows represent the directions in which the images move by the visibility of the eye E to be examined. In FIG. 6, A2, B2 and C2 designate the images when the light source images A1, B1 and C1 on the eye fundus Er are projected onto position sensors 11a, 11b and 11c, respectively, and arrows represent the directions in which the images move by the visibility of the eye E to be examined.

For example, the light beam passed through the aperture 4a of the first three-aperture stop 4 becomes the light source image A1 on the eye fundus Er, is reflected by the eye fundus Er, passes through the aperture 7a of the second three-aperture stop 7, is image-rotated by the image rotating prism 9a and becomes the light source A2 on the one-dimensional light position sensor 11a. From this light beam position, the visibility in the meridian direction passing through the apertures 4a and 7a is found. Also, the light beam passed through the aperture 4b becomes the light source image B1 on the eye fundus Er, and the reflected light thereof passes through the aperture 7b, is image-rotated by the image rotating prism 9b and becomes the light beam B2 on the one-dimensional light position sensor 11b. Further, the light beam passed through the aperture 4c likewise becomes the light beam C2 on the one-dimensional light-position sensor 11c.

If the meridian direction and the direction of one of the position sensors 11a, 11b and 11c are concident with each other, image rotation is not needed with respect to that meridian. Accordingly, in this case, the image rotating prisms by odd number reflections may be provided in the optical paths of the other two meridians.

The visibility in three meridian directions is found from the positions of the light beams A2, B2 and C2 and therefore, the visibility in the other meridian directions can be calculated by regarding it as a sine wave variation, whereby the degree of spherical refraction, the degree of astigmatic refraction and the angle of astigmatism of the eye E to be examined are found. The light-receiving element 10 may be, for example, a CCD (charge coupled device), a semiconductor light-position detector or the like.

The light beams A2, B2 and C2 on the light-receiving element 10 move in a direction perpendicular to the directions of arrows if the eye E to be examined is an astigmatic eye, but they may be directed onto the light-receiving element 10 by the use of a cylindrical lens and only the movement thereof in the directions of arrows may be found. As regards meridian directions, a minimum of three meridian directions are necessary, and the positions and number of the apertures of the first and second three-aperture stops 4 and 7 shown in FIGS. 3 and 4 can be chosen arbitrarily where measurement is effected in three or more meridian directions. For example, if the positions of the apertures are put aside to one side relative to the centers of three-aperture stops 4' and 7' as shown in FIGS. 8 and 9, the apertured mirror 5 in FIG. 1 may be replaced by an ordinary mirror.

FIG. 10 shows a second embodiment using the first and second three-aperture stops 4' and 7' shown in FIGS. 8 and 9. In this embodiment, a mirror 12 employed instead of the apertured mirror 5 of FIG. 1 is disposed at a position opposite to the positions of the apertures of the first three-aperture stop 4' shown in FIG. 8 relative to the optical axis 01, and one side thereof relative to the optical axis 01 reflects light and the other side thereof transmits light therethrough. Generally, the manufacture of an apertured mirror is technically considerably difficult and therefore, if it can be replaced by an ordinary mirror as shown in the embodiments of FIG. 10, its technical and economical effects will be great.

In the above-described embodiments, three one-dimensional light-position sensors arranged in parallel to one another on a substrate can be employed as the light-receiving element and therefore, measurement of eye refraction becomes possible simply by a single light-receiving element and as a result, the structure of the entire apparatus is simplified and the apparatus becomes compact and inexpensive.

A different embodiment will now be described, and FIG. 11 shows the optical arrangement thereof. On the optical axis 01 passing through a light source 21 such as an LED and the fundus Er of the eye E to be examined, a deflecting prism 22, a slit plate 23, a lens 24, an aperture stop 25, a lens 26 and an objective 27 are disposed in succession from the light source 21 side, and a half-mirror 28 is disposed in the light beam below the optical axis 01 between the lens 26 and the objective 27. A lens 29, an aperture stop 30, an image rotating and deflecting prism 31 and a linear photosensor array 32 are disposed on an optical axis 02 reflected by the half-mirror 28.

The deflecting prism 22, as shown in FIG. 12, is comprised of three wedge prisms 22a, 22b and 22c, and a light beam emitted from the light source 21 is divided into three light beams by the wedge prisms 22a, 22b and 22c. FIG. 13 shows the three slits 23a, 23b and 23c of the slit plate 23, and the three light beams divided by the deflecting prism 22 pass through the respective slits 23a, 23b and 23c of the slit plate 23 and are imaged on the aperture stop 25 by the lens 24.

FIG. 14 shows three openings 25a, 25b and 25c formed in the upper half of the aperture stop 25. The light beams passed through the slits 23a, 23b and 23c pass through the corresponding openings 25a, 25b and 25c and are re-imaged on the pupil Ep of the eye E to be examined by the objective lens 27. At this time, the slit plate 23 is disposed so as to be optically conjugate with the fundus Er of the emmetropia eye to be examined by the lens 26 and the objective 27.

The light beam reflected from the eye fundus Er is reflected by the half-mirror 28 for reflecting the light beam below the optical axis 01, and passes through the lens 29 to the aperture stop 30. FIG. 15 shows a front view of the aperture 30. The aperture stop 30 has three openings 30a, 30b and 30c at positions optically conjugate with the aperture stop 25. The light beams passed through these openings 30a, 30b and 30c are rotated and deflected by the image rotating and deflecting prism 31 and are directed onto the single linear photosensor array 32 lying at a position optically conjugate with the slit plate 23. Thus, the light is supplied from one half of the pupil Ep to the eye fundus Er by the aperture stop 25, and the light beam emerging from the other half of the pupil Ep with the aid of the aperture stop 30 is measured, whereby corneal reflection can be avoided.

The image rotating and deflecting prism 31 comprises three small prisms 31a, 31b and 31c (of which the small prisms 31a and 31c are not shown) corresponding to the light beams passed through the openings 30a, 30b and 30c of the aperture stop 30, and the small prism 31b corresponding to the opening 30b is shown in FIG. 16. The image rotating and deflecting prism 31 has the image rotating function and the deflecting function, and the image rotating function is performed by this small prism 31b. That is, as regards the light beam passed through the small prism 31b, when viewed in the plane of the drawing sheet of FIG. 16, the image is inverted in the plane of the drawing sheet and inversion of the image does not take place in a plane perpendicular to the plane of the drawing sheet. When the small prism 31b is rotated by 90° about the optical axis, the direction of the image does not change in the plane of the drawing sheet, but the image is inverted in the plane perpendicular to the plane of the drawing sheet and is rotated by 180°. The present embodiment utilizes the fact that when such a small prism 31b is rotated about the optical axis, the image is rotated about the same axis twice the angle of rotation of the small prism. Also, the deflecting function can be realized by suitably setting the inclinations of the entrance and exit surfaces of the small prism 31b.

In this manner, the light beams passed through the openings 30a, 30b and 30c are rotated and deflected by the small prisms 31a, 31b and 31c and are imaged at predetermined positions on the linear photosensor array 32. As regards a meridian, two small prisms will do if rotation and deflection are not effected.

FIG. 17 shows the reflected images on the linear photosensor array 32 disposed at a predetermined position by the image rotating and deflecting prism 31. The slit image 23A is the image by the light beam passed through the slit 23a and openings 25a, 30a; the slit image 23B is the image by the light beam pass through the slit 23b and openings 25b, 30b; and the slit image 23C is the image by the light beam passed through the slit 23c and openings 25c, 30c.

Now, where the emmetropia providing the reference is the eye to be examined, the reflected images on the linear photosensor array 32 can be disposed at predetermined positions having certain intervals therebetween by suitably selecting the angle of rotation and the angles of the entrance and exit surfaces of the image rotating and deflecting prism 31. If the conditions of the image rotating and deflecting prism 31 are set in this manner and another eye E to be examined is disposed, the positions of the reflected images move in conformity with the difference in refractive power between said another eye E to be examined and the emmetropia in each meridian direction and therefore, the positions of the reflected images 23A, 23B and 23C provide the data for knowing the respective refractive powers. That is, the value of refraction in the direction of the openings 25a, 30a is found from the position of the reflected image 23A, and the values of refraction in the direction of the openings 25b, 30b and the direction of the openings 25c, 30c, respectively, are found from the positions of the reflected images 23B and 23C.

Now, the variation in the value of refraction of an eye in the meridian directions is considered to be sine-wave-like and therefore, if the value of refraction in three meridian directions is found, the value of refraction in the other meridian directions can also be calculated, and the value of refraction, i.e., the degree of sphericity, the degree of astigmatism and the angle of astigmatism, of the eye E to be examined can be calculated.

FIG. 18 shows an embodiment in which three light sources 24a, 24b and 24c are disposed instead of the light source 21, and these light sources are adapted to be turned on successively. In this embodiment, the three light sources 24a, 24b and 24c are provided and therefore, the deflecting prism 22 for dividing the light beam into three directions may be eliminated, but excepting the deflecting prism 22, the angles of the entrance and exit surfaces of an image rotating and deflecting prism 31 and the length of a linear photosensor array 32 are only fluctuated and in the other points, the construction of this embodiment is similar to that of the embodiment of FIG. 11.

The three light sources 24a, 24b and 24c are successively turned on and illuminate the three slits 23a, 23b and 23c, respectively, of the slit plate 23, and as shown in the embodiment of FIG. 11, three slit images are successively formed on the linear photosensor array 32. Since the three slit images are formed on the linear photosensor array 32 not at a time but successively in this manner, it is not necessary to shift the positions of the three slit images as shown in the embodiment of FIG. 11. If the angles of the entrance and exit surfaces of the image rotating and deflecting prism 31 are adjusted so that reflected images in three meridian directions may be formed at the same position on the linear photosensor array 32 when the three light sources 24a, 24b and 24c are successively turned on relative to the emmetropia which provides the reference, the refractive powers in the three meridian directions can be found from the deviation of the reflected images in the three meridian directions from the reference position when the eye E to be exposed is disposed.

In this embodiment, as compared with the embodiment of FIG. 11, the number of light source must be increased, but instead, the number of the slit images on the sensor array 32 can be one and therefore, the length of the sensor array can be shortened.

Figure 19:
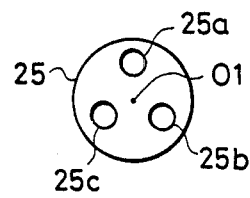
FIGS. 19 and 20 are front views of aperture stops according to further embodiments.
Figure 20:
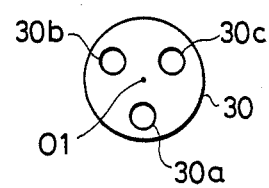

As an aperture stop 25, three openings 25a, 25b and 25c may be disposed at equal intervals as shown in FIG. 19, and an aperture stop 30 may have openings 30a, 30b and 30c provided at positions symmetrical with the openings 25a, 25b and 25c about the optical axis 01 as shown in FIG. 20. In this case, however, an apertured mirror may preferably be used instead of the half-mirror 28.

Figure 21:
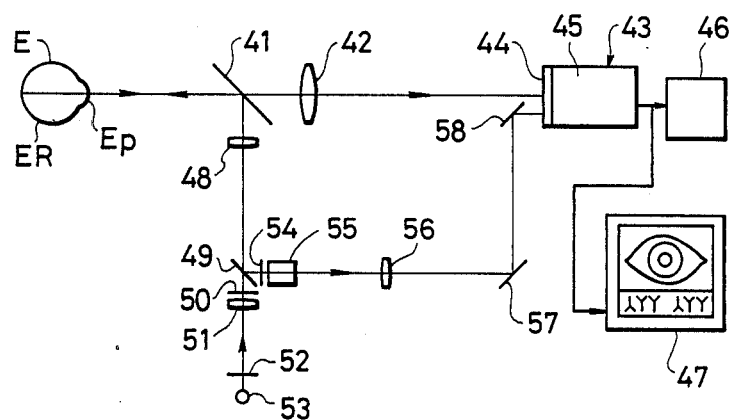
FIG. 21 shows the optical arrangement of an embodiment using a television for observing an eye to be examined for measurement.

FIG. 21 and the following drawings show an embodiment using the scanning lines of a television for observing an eye to be examined for measurement.

In FIG. 21, letter E designates an eye to be examined, ER denotes the fundus of the eye E to be examined, and Ep designates the pupil of the eye E to be examined. Before the eye E to be examined, a light dividing member 41, a lens 42 and a TV camera 43 are disposed in succession from the eye E side. The TV camera 43 comprises an area sensor array 44 which is an image pickup device such as a two-dimensional CCD and a reflex unit 45, and the reflex video signal thereof is supplied to a signal processing unit 46 and a TV monitor 47. A lens 48, an apertured mirror 49, an entrance stop 50, a lens 51, a pattern stop 52 and a measuring light source 53 are arranged in succession on the reflection side of the light dividing member 41. An exit stop 54, an image rotating and deflecting prism 55 and a lens 56 are disposed on the reflection side of the apertured mirror 49, and a light beam reflected by the apertured mirror 49 may enter the TV camera 43 via mirrors 57 and 58.

Figure 22:
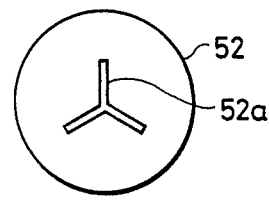
FIG. 22 is a front view of a pattern stop.
Figure 23:
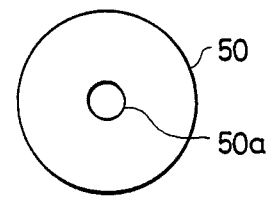
FIG. 23 is a front view of an entrance stop.

In FIG. 21, light emitted from the measuring light source 53 illuminates the pattern stop 52 disposed at a position optically conjugate with the fundus of the emmetropia. This pattern stop 52 has a pattern 52a comprising three radially arranged slit openings as illustrated in FIG. 22, and the light beams passed through these slit openings project the pattern 52a from the center of the pupil Ep of the eye E to be examined onto to eye fundus Er through the entrance stop 50 having a circular opening 50a centrally thereof as illustrated in FIG. 23, the apertured mirror 49 formed with an aperture centrally thereof, the lens 48 and the light dividing member 41.

Figure 24:
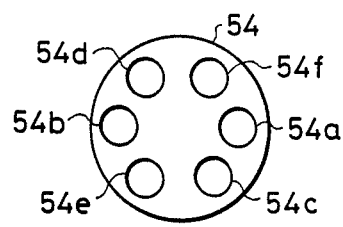
FIG. 24 is a front view of an exit stop.
Figure 25:
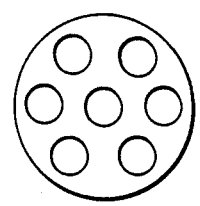
FIG. 25 illustrates the incident and emergement light beams on the pupil.

Part of the reflected light from the eye fundus ER passes through the light dividing member 41, the lens 48 and the apertured mirror 49 and through the exit stop 54 having six openings 54a-54f therein as shown in FIG. 24, and projects the slit image from the eye fundus onto the area sensor array 44 which is an image pickup device through the image rotating and deflecting prism 55, the lens 56 and the mirrors 57, 58. In the present embodiment, the incident and emergent light beams on the pupil are such as shown in FIG. 25.

On the other hand, the observation light for alignment travels rectilinearly through the light dividing member 41 and images the front eye part of the eye E to be examined on the area sensor array 44 by the lens 42. In this case, an external eye illuminating light source may be provided discretely from the measuring light source 53. In the present embodiment, the observation light and the measuring light are adapted to enter the different regions of the area sensor array 44, but a further light dividing member may be interposed to divide the light in time and cause the divided lights to successively enter the same region of the area sensor array 44. The light dividing member 41 may efficiently be a dichroic mirror of wavelength selecting property.

The TV camera 43 for making the signal from the area sensor array 44 into an image video signal by the reflex unit 45 transmits the image video signal to the image processing unit 46 and the TV monitor 47 and causes it to be displayed thereby. The measurement signal may be taken out directly from the area sensor array. In that case, a signal for each bit is obtained and therefore, the accuracy becomes high.

Figure 26:
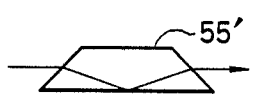
FIG. 26 is a cross-sectional view of an image rotating prism.
Figure 27:
FIG. 27 is a cross-sectional view of a deflecting prism.
Figure 28:
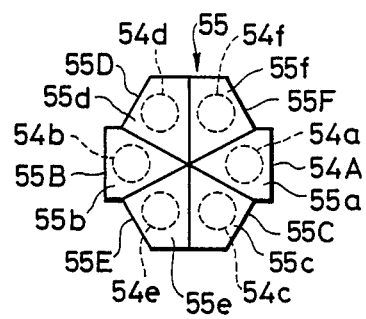
FIG. 28 is a cross-sectional view of a rotating and deflecting prism.

The image rotating and deflecting prism 55 comprises a combination of an image rotating prism 55' shown in FIG. 26 and a deflecting prism 55" shown in FIG. 27. FIG. 28 shows a cross-section of this image rotating and deflecting prism 55, and as shown, the image rotating and deflecting prism is comprised of six small prisms 55a-55f corresponding to the six openings 54a-55f of the exit stop 54. For example, the light beam passed through the opening 54c of the exit stop 54 enters the small prism 55c and is totally reflected by the reflecting surface 55C thereof. The reflecting surface 55C is inclined by 30° with respect to the reflecting surface 55A of the small prism 55a and therefore, the image is rotated by 60°. The openings of the exit stop 54 are arranged at meridian intervals of 60°, and to measure the value of refraction in the meridian direction passing through the openings 54c and 54d, the inclinations of two light beams having gone out therefrom may be measured. In this case, if the eye to be examined is an emmetropia, the two light beams become parallel to each other, and by these light beams being passed through the image rotating and deflecting prism 55, the movement toward the openings 54c and 54d can be changed into the movement toward the openings 54a and 54b. Likewise, the value of refraction in the meridian direction passing through the openings 54f and 54e can be measured as the meridian direction passing through the openings 54a and 54b. The light beams passed through the openings 54a and 54b need not be rotated and therefore, the small prisms 55a and 55b can be eliminated.

The deflecting prism 55" serves to separate the six images passed through the six openings from one another at a suitable interval, and by suitably choosing the angle of inclination of the end surface of the rotating prism 55', the deflecting prism 55" and the rotating prism 55' can be made integral with each other.

Figure 29:
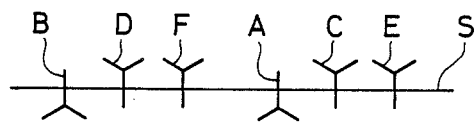
FIG. 29 illustrates the eye fundus pattern image on an area sensor array.

FIG. 29 shows the six images A-F on the area sensor array 44. The images A-F have been formed by the light beams passed through the openings 54a-54f. The values of refraction in three meridian directions can be found from the intervals on a scanning line S between these three sets of images A and B, C and D, and E and F. Generally, the value of refraction of an eye is considered to vary in a sine-wave-like fashion relative to the meridian direction and therefore, if the values of refraction in three meridian directions are known, the values of refraction in the other meridian directions can be found by calculation and thus, the degree of spherical refraction, the degree of astigmatism and the angle of astigmatism can be calculated.

To find the positions of the respective images on the scanning line S, a method of setting a threshold value of a suitable level by a video signal and transforming it into a binary form of a method of A/D-converting a signal for each bit, entering the converted signal into a memory and calculating the same can be adopted. If averaging is effected by the use of signals on a plurality of scanning lines instead of the signal on the single scanning line S, noise will be averaged and therefore, the accuracy of measurement can be improved.

The TV camera may be a conventional TV camera using not an area array sensor but an image pickup tube as the image pickup device.

It is also possible to use an image rotating prism instead of the image rotating and deflecting prism 55 and effect the measurement by three parallel scanning lines as shown in FIG. 6.

We claim:
1. An apparatus for measuring the refractive power of an eye having:
   a target projecting system having no moving parts for projecting a target onto a fundus of an eye to be examined through a predetermined optical path of a pupil of the examined eye;
   light-receiving optical means for receiving light beams reflected by the eye fundus through paths corresponding to at least three meridian directions of the pupil other than said predetermined path, said light-receiving optical system having a plurality of image rotating prisms for rotating the meridian direction of each respective each light beam into a predetermined direction common with the other respective light beams; and light detecting means for detecting the position of each eye fundus reflection light beam in said predetermined common direction and determining the refractive power of an examined eye.

2. An apparatus according to claim 1, wherein said light detecting means comprises three one-dimensional light-position sensors disposed parallel to one another on a light detecting element.

3. An apparatus according to claim 1, wherein said image rotating prisms also deflect the eye fundus reflection light beam, and said light detecting means is a single one-dimensional light-position sensor.

4. An apparatus according to claim 1, wherein said target projecting means projects the target light beam from an eccentric position on at least three meridians of the pupil of the eye to be examined, and said light-receiving optical means receives the light beam reflected by the eye fundus from a position symmetrical with an incidence position with respect to a center of the pupil.

5. An apparatus according to claim 1, wherein said target projecting means projects the target light beam to a center of the pupil, and said light-receiving optical means receives the light beam reflected by the eye fundus from two positions symmetrical with respect to the center of the pupil in three meridian directions.

6. An apparatus according to claim 1, wherein said target projecting means and said light-receiving optical means are each provided with an apertured stop optically conjugate with the pupil of the eye to be examined.

7. An apparatus according to claim 1, wherein an apertured mirror is provided at a branching-off position of the optical path of said target projecting means and said light-receiving optical means.

8. An apparatus according to claim 1, wherein a mirror for at least reflecting only the light beam on one side of an optical axis and transmitting therethrough the light beam on the other side of said optical axis is provided at a branching-off position of the optical path of said target projecting means and said light-receiving optical means.

9. An apparatus according to claim 1, wherein said target projecting means system is provided with a light source, a deflecting prism having three wedge prisms, a slit plate having three slits, and an apertured stop disposed at a position optically conjugate with the pupil of the eye to be examined and having three openings at locations spaced apart from a center portion thereof.

10. An apparatus according to claim 1, wherein said image rotating prisms are disposed in two meridian directions.

11. An apparatus according to claim 3, wherein said light detecting means receives the light beams reflected by the eye fundus in three meridian directions at a time.

12. An apparatus according to claim 3, wherein said light detecting means receives the light beams reflected by the eye fundus in three directions in succession.

13. An apparatus for measuring the refractive power of an eye having:
    target projecting means having no moving parts for projecting a target onto a fundus of an eye to be examined through a predetermined optical path of a pupil of the examined eye;
    a light-receiving optical means for receiving light beams reflected by the eye fundus through paths corresponding to at least three meridian directions of the pupil other than said predetermined path direction, said light-receiving optic means having a plurality of image rotating prisms for rotating the meridian direction of each respective light beam into a predetermined direction common with the other respective light beams; and
    a television camera with an image pickup element for detecting the position of each eye fundus reflection light beam in said predetermined common direction and determining the refractive power of the examined eye, wherein an interior part of the eye to be examined is observed by said television camera.

14. An apparatus according to claim 13, wherein an apertured mirror is provided at a branching-off position of the optical path of said target projecting means and said light-receiving optical means.

15. An apparatus according to claim 14, wherein a light dividing member is disposed in the optical path between said apertured mirror and the eye to be examined, and the anterior part of the eye to be examined is observed through said light dividing member.

* * * * *

UNITED STATES PATENT AND TRADEMARK OFFICE
CERTIFICATE OF CORRECTION

PATENT NO. : 4,820,037
DATED : April 11, 1989
INVENTOR(S) : YOSHIMI KOHAYAKAWA, ET AL.   Page 1 of 3

It is certified that error appears in the above-identified patent and that said Letters Patent is hereby corrected as shown below:

Title page:

IN [56] REFERENCES CITED

FOREIGN PATENT DOCUMENTS, "56-161031  5/1980  Japan."
       should read --56-161031  12/1981  Japan.--.

IN [57] ABSTRACT

"15 Claims, 29 Drawing Sheets" should read
       --15 Claims, 4 Drawing sheets--.

COLUMN 2

Line 17, "emergement" should read --emergent--.
   Line 34, "and" should read --a--.
   Line 59, "aperture" should read --apertures--.

COLUMN 3

Line 43, "concident" should read --coincident--.

COLUMN 5

Line 43, "pass" should read --passed--.

COLUMN 6

Line 43, "light source" should read --light sources--.

UNITED STATES PATENT AND TRADEMARK OFFICE
CERTIFICATE OF CORRECTION

PATENT NO. : 4,820,037
DATED : April 11, 1989
INVENTOR(S) : YOSHIMI KOHAYAKAWA, ET AL.    Page 2 of 3

It is certified that error appears in the above-identified patent and that said Letters Patent is hereby corrected as shown below:

COLUMN 7

Line 16, "eye fundus Er" should read --eye fundus ER--.
   Line 59, "six openings 54a-55f" should read
            --six openings 54a-54f--.

COLUMN 8

Line 64, "light-receiving optical system" should read
            --light-receiving optical means--.

COLUMN 9

Line 38, "optical axis" should read --optic axis--.
   Line 39, "optical axis" should read --optic axis--.
   Line 44, "system" should be deleted.

UNITED STATES PATENT AND TRADEMARK OFFICE
CERTIFICATE OF CORRECTION

PATENT NO. : 4,820,037
DATED : April 11, 1989
INVENTOR(S) : YOSHIMI KOHAYAKAWA, ET AL.    Page 3 of 3

It is certified that error appears in the above-identified patent and that said Letters Patent is hereby corrected as shown below:

COLUMN 10

Line 33, "interior" should read --anterior--.

Signed and Sealed this

Twentieth Day of March, 1990

Attest:

JEFFREY M. SAMUELS

*Attesting Officer*    *Acting Commissioner of Patents and Trademarks*